(12) United States Patent
Huang et al.

(10) Patent No.: US 8,003,344 B2
(45) Date of Patent: Aug. 23, 2011

(54) MICROBIAL HYDROGEN-PRODUCING PROCESS AND SYSTEM THEREOF

(75) Inventors: Chieh-Chen Huang, Taichung (TW); Jui-Jen Chang, Taichung (TW); Cheng-Yu Ho, Taichung (TW); Wei-En Chen, Taichung (TW); Jiunn-Jyi Lay, Kaohsiung (TW); Chia-Hung Chou, Kaohsiung (TW); Chang-Lung Han, Tainan (TW)

(73) Assignee: National Chung Hsing University, Taichung (TW)

( * ) Notice: Subject to any disclaimer, the term of this patent is extended or adjusted under 35 U.S.C. 154(b) by 549 days.

(21) Appl. No.: 12/068,050

(22) Filed: Feb. 1, 2008

(65) Prior Publication Data

US 2009/0035812 A1      Feb. 5, 2009

(30) Foreign Application Priority Data

Aug. 3, 2007   (TW) .............................. 96128765 A

(51) Int. Cl.
*C12P 39/00*      (2006.01)
*C12P 3/00*       (2006.01)

(52) U.S. Cl. .................. 435/42; 435/168; 435/290.1
(58) Field of Classification Search .................. None
See application file for complete search history.

(56) References Cited

U.S. PATENT DOCUMENTS

| | | | | |
|---|---|---|---|---|
| 4,737,459 | A * | 4/1988 | Zeikus et al. | 435/162 |
| 4,973,559 | A * | 11/1990 | Dexter et al. | 435/252 |
| 5,648,264 | A * | 7/1997 | Kume | 435/264 |
| 5,733,741 | A * | 3/1998 | Kume | 435/67 |
| 7,176,005 | B2 * | 2/2007 | Melis et al. | 435/168 |
| 2007/0207531 | A1 * | 9/2007 | Ferchichi et al. | 435/168 |

* cited by examiner

*Primary Examiner* — Herbert J. Lilling
(74) *Attorney, Agent, or Firm* — Bacon & Thomas, PLLC

(57) ABSTRACT

The present invention provides a microbial hydrogen-producing process, comprising: providing at least one *Clostridium* microbe and at least one *Bacillus* microbe; and co-culturing said at least one *Clostridium* microbe and said at least one *Bacillus* microbe in a fermentation culture system to produce hydrogen. The present invention also provides a microbial hydrogen-producing system, characterized by that the system comprises at least one *Clostridium* microbe and at least one *Bacillus* microbe, and it uses an organic waste medium as the substrate to perform a hydrogen-producing fermentation having high efficiency, high stability, and high reproducibility.

12 Claims, 5 Drawing Sheets

MICROBIAL HYDROGEN-PRODUCING PROCESS AND SYSTEM THEREOF

BACKGROUND OF THE INVENTION

1. Field of the Invention

The present invention relates to a microbial hydrogen-producing process having high efficiency, high stability, and high reproducibility, which co-culturing at least one *Clostridium* microbe and at least one *Bacillus* microbe in a fermentation culture system to produce hydrogen.

2. Description of the Related Art

In recent years, the excessive consumption of fossil fuel has caused energy shortage and global climate change; therefore, more and more attentions are attracted to the alternative energy resources, in which hydrogen and ethanol are focused. To solve this problem, some researchers have suggested using renewable biomass resources as energy resources, thus and so, the problems caused by organic waste can also be solved (Lay 2000; Lay 2001). Since then, the bio-energy production from wastewater or solid waste by microbial fermentation has been considered as an environmentally friendly energy-producing process.

Hydrogen can be produced by water electrolysis, but the electricity cost is high. Although solar-powered water electrolysis equipments are used to produce hydrogen, it is not able to be popularized because the solar energy supply is unstable and the equipments are expensive. Thus, the microbial hydrogen production has been studied from 1970s. Hydrogen-producing microbes are generally comprised in anaerobes, facultative anaerobes, aerobes and photosynthetic bacteria comprise. In these microbes, hydrogenase is involved in many metabolic processes, which not only oxidizes hydrogen gas to hydrogen ions and electrons, but also reduces hydrogen ions and electrons to hydrogen gas ($H_2 \leftrightarrows 2H^+ + 2e^-$); however, its regulation mechanism is still needed to be further studied.

The traditional hydrogen-producing fermentation chamber is a complicated open system composed of a variety of bacteria and the operation of this system is not stable. In addition, the conventional screening method cannot effectively identify the hydrogen-producing microbes, because the bacteria predominant in number may not the bacteria having hydrogen-producing capacity, and it is difficult to estimate the hydrogen-producing contribution of each screened bacterium. In addition, microbes from the same genus but different species may have different hydrogen-producing capacity, even microbes from the same species may have completely different hydrogen-producing capacity because they are obtained from different sources and belong to different strains. This is a great difficulty with which the microbial hydrogen-producing researchers have faced.

It has been known that the acetone-butanol-ethanol fermentation (ABE fermentation) of *Clostridium* microbes transfers carbohydrates to acetone, butanol and ethanol, and produces hydrogen at the same time. *Clostridium beijerinckii*, which is utilized in the current studies, has an exceptional ABE fermentation performance (Shaheen et al., 2000). *Clostridium beijerinckii* can decompose carbohydrates released from a variety of plants (Ezeji et al., 2007), but it is not economical because hydrolysis must be performed before fermentation. On the other hand, *Bacillus* microbes have been applied to the environmental sanitation industry to decompose complicated insoluble substances to soluble monomers for a long time (Clerek et al., 2004). Specifically, *Bacillus thermoamylovorans* is an important microbe in the compost, and it can transfer sludge and food waste into an organic fertilizer (Ivanov et al., 2004; Wang et al., 2003). However, no study shows the way how to apply these bacteria to hydrogen production of organic wastes, and how to develop an energy system for clean energy production and resources regeneration.

SUMMARY OF THE INVENTION

To solve the above-mentioned problems, one object of the present invention is to provide a hydrogen-producing process, which comprises co-culturing at least one *Clostridium* microbe and at least one *Bacillus* microbe in a fermentation culture system to produce hydrogen. In coordination with waste regeneration, the present invention can solve parts of waste treatment problems, and it responses to the trend of energy development in the future.

More specifically, the object of the present invention is to provide a fermentation system, in which co-culturing at least one *Clostridium* microbe and at least one *Bacillus* microbe in a medium produced by an organic waste.

To achieve these objects, the present invention provides a microbial hydrogen-producing process, comprising: providing at least one *Clostridium* microbe and at least one *Bacillus* microbe; and co-culturing said at least one *Clostridium* microbe and said at least one *Bacillus* microbe in a fermentation culture system to produce hydrogen.

In the preferred embodiments, said at least one *Clostridium* microbe comprises *C. beijerinckii* L9 deposited with Food Industry Research and Development Institute under the accession number BCRC910361 on Jul. 27, 2007 or *C. butyricum* M1 deposited with Food Industry Research and Development Institute under the accession number BCRC910362 on Jul. 27, 2007.

In the more preferred embodiments, said at least one *Clostridium* microbe is *C. beijerinckii* L9.

In the preferred embodiments, wherein said at least one *Bacillus* microbe is *B. thermoamylovorans* I deposited with Food Industry Research and Development Institute under the accession number BCRC910360 on Jul. 27, 2007.

In the preferred embodiments, said fermentation culture system is a fermentation system having a sterile and anaerobic environment; more preferably, a fermentation system having a sterile and anaerobic environment and using an organic waste medium; and most preferably, a batch fermentation system having a sterile and anaerobic environment and using an organic waste medium.

In the preferred embodiments, said organic waste medium is a medium produced from yeast waste, distillers grains, kitchen waste, sewage sludge, agricultural waste (ex. straw or bagasse), molasses and its fermented waste liquid, energy crop (ex. sweet potato or napiergrass), algae, or mixtures thereof; more preferably, a medium produced from yeast waste.

In the preferred embodiments, said anaerobic environment is formed by the interaction between said at least one *Clostridium* microbe and said at least one *Bacillus* microbe.

In the more preferred embodiments, an additional sterile and/or anaerobic environment is further applied.

In the preferred embodiments, fermentation is performed at 35-45° C. in said fermentation culture system; more preferably, at 40° C.

The present invention also provides a microbial hydrogen-producing process, characterized by: co-culturing at least one *Clostridium* microbe and at least one *Bacillus* microbe in a medium produced from yeast waste under a sterile and anaerobic environment in a fermentation system to produce hydrogen.

In the preferred embodiments, said fermentation system is a batch fermentation system.

In the more preferred embodiments, said fermentation system is further a fermentation system having a sterile environment.

In the preferred embodiments, said at least one *Clostridium* microbe comprises *C. beijerinckii* L9 or *C. butyricum* M1; more preferably, *C. beijerinckii* L9.

In the preferred embodiments, said at least one *Bacillus* microbe is *B. thermoamylovorans* I.

In the preferred embodiments, said anaerobic environment is formed by the interaction between said at least one *Clostridium* microbe and said at least one *Bacillus* microbe.

In the more preferred embodiments, an additional sterile and/or anaerobic environment is further applied.

In the preferred embodiments, alcohol products and acid products are produced in the process. More preferably, said alcohol products comprises ethanol, which can be used as an energy substitute and an industrial raw material; and said acid products comprises butanoic acid, which is a common raw material in chemical industries.

The present invention yet provides a microbial hydrogen-producing system, comprising: at least one *Clostridium* microbe and at least one *Bacillus* microbe; and an organic waste medium.

In the preferred embodiments, said at least one *Clostridium* microbe comprises *C. beijerinckii* L9 or *C. butyricum* M1; more preferably, *C. beijerinckii* L9.

In the preferred embodiments, said at least one *Bacillus* microbe is *B. thermoamylovorans* I.

In the more preferred embodiments, said anaerobic environment is formed by the interaction between said at least one *Clostridium* microbe and said at least one *Bacillus* microbe.

In the preferred embodiments, said system is a batch fermentation system.

In the more preferred embodiments, said system has a sterile and/or anaerobic environment.

In the preferred embodiments, said organic waste medium is a medium produced from yeast waste, distillers grains, kitchen waste, sewage sludge, agricultural waste (ex. straw or bagasse), molasses and its fermented waste liquid, energy crop (ex. sweet potato or napiergrass), algae, or mixtures thereof; more preferably, a medium produced from yeast waste.

In the preferred embodiments, alcohol products and acid products are produced in the process. More preferably, said alcohol products comprises ethanol, which can be used as an energy substitute and an industrial raw material; and said acid products comprises butanoic acid, which is a common raw material in chemical industries.

From above, the present invention provides a process for co-culturing at least one *Clostridium* microbe and at least one *Bacillus* microbe in a fermentation culture system to produce hydrogen. In comparison with the traditional hydrogen production in an open system, the present process can effectively enhance the hydrogen-producing efficiency and regenerate the waste-resource, which answer to green production and sustainable development.

BRIEF DESCRIPTION OF THE DRAWINGS

FIG. 1(*b*) shows the produced-hydrogen accumulation curve obtained from *C. beijerinckii* L9 (◯), *C. diolis* Z2 (Δ), *C. roseum* Z5-1 (⋈) and *C. roseum* W8 (Δ) cultured in a non-sterile yeast waste medium under an non-anaerobic environment.

FIG. 2(*a*) represents the produced-hydrogen accumulation curve obtained from *C. beijerinckii* L9 and B. thermoamylovorans I co-cultured under a sterile and non-anaerobic environment.

FIG. 2(*b*) represents the produced-hydrogen accumulation curve obtained from *C. beijerinckii* L9 cultured under a sterile and anaerobic environment.

FIG. 2(*c*) represents the produced-hydrogen accumulation curve obtained from compost cultured under a non-sterile and non-anaerobic environment.

FIG. 2(*d*) represents the produced-hydrogen accumulation curve obtained from the batch fermentation culture medium cultured under a non-sterile and non-anaerobic environment.

FIG. 3(*b*) shows the volatile fatty acids (VFA) concentration obtained from *C. beijerinckii* L9 and *B. thermoamylovorans* I co-cultured in yeast waste medium under a sterile and non-anaerobic environment.

FIG. 3(*c*) shows the alcohol concentration obtained from *C. beijerinckii* L9 and *B. thermoamylovorans* I co-cultured in yeast waste medium under a sterile and non-anaerobic environment.

FIG. 3(*d*) shows the cfu/mL obtained from *C. beijerinckii* L9 and *B. thermoamylovorans* I co-cultured in yeast waste medium under a sterile and non-anaerobic environment.

FIG. 4(*a*) represents the produced-hydrogen accumulation volume obtained from the batch fermentation cultures of *C. butyricum* M1 (◯), compost (□) and yeast waste medium without adding any additional bacteria (Δ) in a sterile and anaerobic yeast waste medium.

FIG. 4(*b*) represents the hydrogen gas concentration obtained from the batch fermentation cultures of *C. butyricum* M1 (◯), compost (□) and yeast waste medium without adding any additional bacteria (Δ) in a sterile and anaerobic yeast waste medium.

FIG. 4(*c*) represents the hydrogen-producing rate obtained from the batch fermentation cultures of *C. butyricum* M1 (◯), compost (□) and yeast waste medium without adding any additional bacteria (A) in a sterile and anaerobic yeast waste medium.

FIG. 5(*b*) shows the produced-hydrogen accumulation curve obtained from *C. butyricum* M1 cultured alone under a sterile and anaerobic environment.

DETAILED DESCRIPTION OF THE PREFERRED EMBODIMENTS

Figure 1:
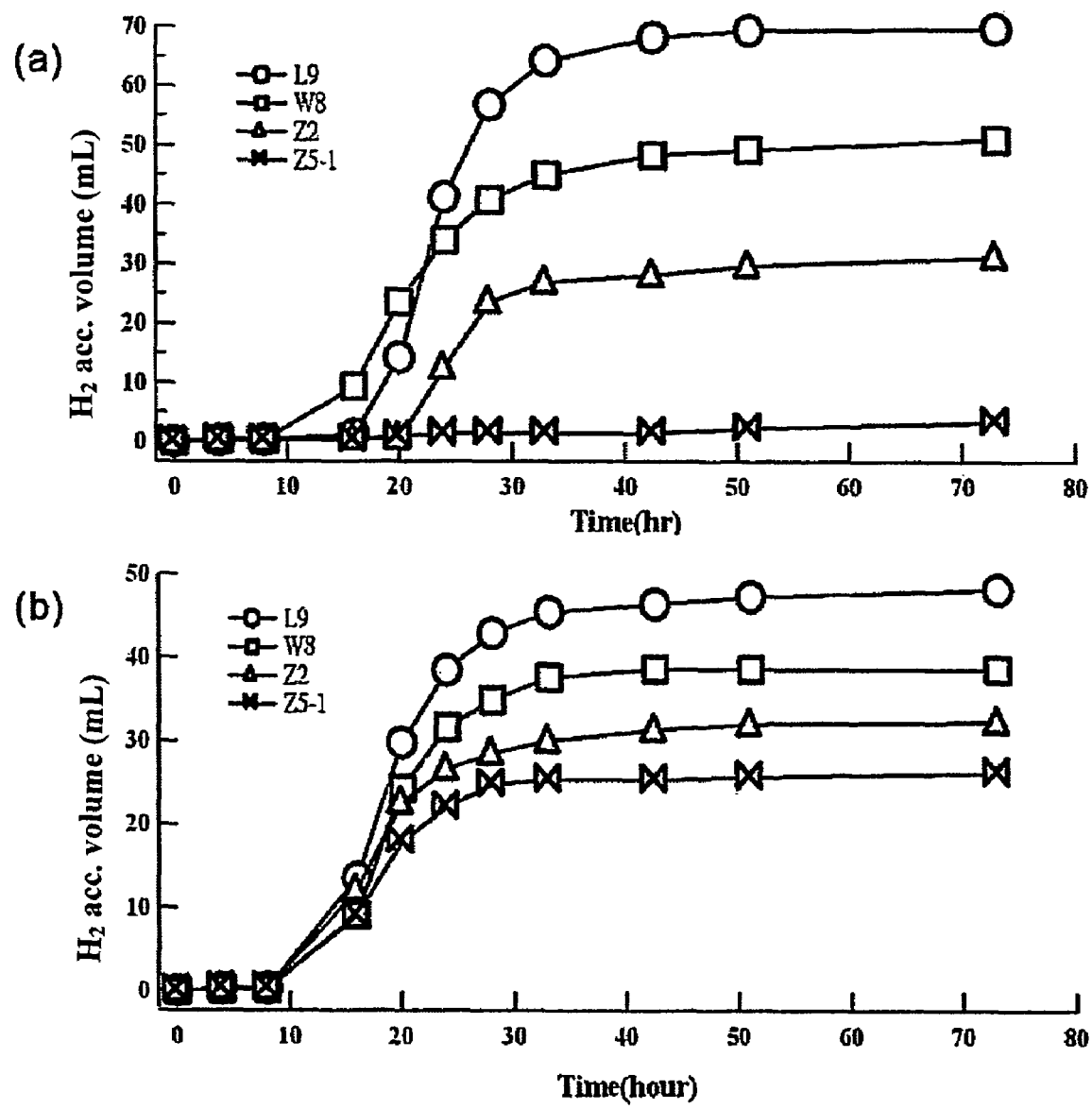
FIG. 1(*a*) shows the produced-hydrogen accumulation curve obtained from *C. beijerinckii* L9 (◯), *C. diolis* Z2 (Δ), *C. roseum* Z5-1 (⋈) and *C. roseum* W8 (□) cultured in a sterile yeast waste medium under an anaerobic environment.

The present invention is based on an unexpected result that co-culturing at least one *Clostridium* microbe and at least one *Bacillus* microbe in a enhances hydrogen-producing efficiency through various interactions between these two microbes. The preferred conditions of the hydrogen-producing process of the present invention are obtained through long-term experiments.

The following examples are only exemplified as the best embodiments, not intended to limit the scope of the present invention. Those skilled in the art can make appropriate changes and modifications according the disclosure hereinafter without departing from the spirit of the present invention.

EXAMPLES

Preparation of Yeast Waste Medium 18.75 g of brewery yeast waste dry powder, 80 g of $NH_4HCO_3$, 40 g of $KH_2PO_4$, 0.4 g of NaCl, 0.11 g of $FeCl_2$, 4 g of $MgSO_4.7H_2O$, 0.4 g of $Na_2MoO_42H_2O$, 0.4 g of $CaCl_2.2H_2O$ and 0.6 g of $MnSO_4.7H_2O$ were added into 1 liter of water and mixed well to obtain a yeast waste medium. This yeast waste medium can be further subjected to a sterilization treatment or an anaerobic treatment by $N_2$ flush in accordance with culture conditions hereinafter.

Inoculum

Compost-derived microbes were used as the inoculum. 64 g of compost prepared by waste rice straw and cattle dung was suspended in 64 mL of water, inoculated to 80 mL of yeast waste medium, and cultured at 40° C. for 12 hours with shaking at 200 rpm under a nitrogen environment. Next, 1 mL of the culture was taken out and heated for 15 minutes in a 85° C. waterbath to kill the non-endospore forming cells, inoculated to 10 mL of liquid PYG medium supplemented with 5 g of peptone, 5 g of tryptone, 10 g of yeast extract, 0.5 g of cysteine HCl, 1.1 mg of $FeSO_4$, 10 mg of resazurin, 0.0082 g of anhydrous $CaCl_2$, 0.019248 g of $MgSO_4.7H_2O$, 21.04 g of $K_2HPO_4$, 21.04 g of $KH_2PO_4$, 0.410 g of $NaHCO_3$, 0.082 g of NaCl, 10 g of glucose and 0.25 g of glutathione, and cultured at 40° C. for 16 hours under a nitrogen environment. This culture was transferred as above for five times, and the enriched culture was serially diluted by PYG medium. After that, the diluted cultures were spread on solid PYG plate comprising 1.5% agar, and placed in GasPak jar (BBL GasPak 100™) for anaerobic culture. After colonies of the inoculum were formed, one single colony grew on the solid PYG plate was isolated and transferred into 80 mL of liquid PYG medium, cultured at 40° C. overnight (16 hours) under a nitrogen environment, and prepared for the following PCR and RT-PCR analysis.

The culture was centrifuged at 2,000 g for 5 minutes to remove solid residues, then centrifuged again at 8,000 g for 5 minutes. The obtained bacterial pellet was washed by 750 µL STE buffer [10 mM Tris-HCl (pH 8.0), 1 mM ethylenediamine tetraacetic acid and 0.1 M NaCl], then re-suspended in 150 µl, S I buffer further comprising 5 mg/mL lysozyme and kept the bacterial suspension at 37° C. for 30 minutes. The bacterial suspension was homogenized by Mini-Beadbeater (Biospec Products, Bartlesville, Okla.), and the bacterial genomic DNA was obtained by Ultraclean Soil DNA Isolation Kit (Mo Bio Laboratories, USA). The impurities in said genomic DNA sample were removed by Micro-Elute DNA Clean/Extraction Kit (GeneMark, Taiwan). In addition, RNase Mini Kit (Qiagen, USA) was used to obtain a RNA sample, and DNA residues in this RNA sample were removed by RQI DNase system (Promega, USA).

Two sets of primers shown in table 1, 16Sf/16Sr and Ef/Er, and the obtained genomic DNA and RNA samples were used for PCR and RT-PCR as below to amplify the 16S rRNA genes and hygrogenase gene included in the genomic DNA and RNA.

RT-PCR was performed by AccessQuick RT-PCR System (Promega) and the obtained RNA sample by the following steps: initially, keeping at 45° C. for 45 minutes, then heating to 95° C. for 2 minutes; subsequently, processing the cycle reaction (95° C. for 30 seconds; 55° C. for 30 seconds; and 68° C. for 1 minutes) for 30-35 cycles; after that, keeping at 68° C. for 7 minutes, and then at 8° C. for 99 minutes. On the other hand, PCR was performed by the following steps: heating at 94° C. for 3 minutes, then processing the cycle reaction (94° C. for 30 seconds; 50° C. for 1 minutes; and 72° C. for 1 minutes) (TAKARA BIO Inc. Shiga, Japan). The obtained DNA products were cloned into a plasmid pGEM-T (Promega Biotech), and sequenced by ABI automated DNA sequencer using Prism dideoxy terminator cycle sequencing kit (Applied Biosystems, Ltd.). At last, the obtained sequence was aligned with the bacterial gene sequences from GenBank by BLAST software to identify the hydrogen-producing bacteria.

TABLE 1

| primer | sequence | specificity | reference |
|---|---|---|---|
| 16Sf | 5'-GCCACGAGCCGCGGT-3' | universal | Lane et al., |
| 16Sr | 5'-ACGGGCGGTGTGTAC-3' | 16S rRNA | 1985 |
| Ef | 5'-GCTGATATGACAATAATGGAAGAA-3' | hygrogenase | Chang et al., |
| Er | 5'-GCAGCTTCCATAACTCCACCGGTTGCACC-3' | | 2006 |

Through PCR and alignment, the predominant hydrogen-producing bacteria were screened out, namely, *Clostridium* microbes, including *C. beijerinckii* L9, *C. diolis* Z2, *C. roseum* Z5-1 and *C. roseum* W8. Also, a facultative *Bacillus* anaerobe, *B. thermoamylovorans* 1, was also found. In the fermentation system, *B. thermoamylovorans* 1 is the only predominant microbe having both protease and α-amylase activities.

These bacteria were inoculated into yeast waste medium and grew at 40° C. under a nitrogen environment. During the growth, gas samples of each experiment group were collected from the culture bottles by plastic syringes and injected into GC-TCD (GC-8A gas chromatograph, Shimadzu do Brasil Comércio Ltda.) for detecting the amount of produced hydrogen; in addition, the concentrations of volatile fatty acids (VFA) and alcohols in these gas samples were detected by GC-FID of the same company.

In the following tests, one single colony of each bacterium was inoculated into liquid PYG medium and grew for approximately 12 hours to log phase. When the $OD_{600}$ of the culture reached 2.0, 4 mL of the bacterial culture was added into 80 mL yeast waste medium, and shook at 200 rpm and 40° C. under a nitrogen environment to perform batch fermentation culture. Associated values were detected. If two bacteria were co-cultured, 2 mL of each bacterial culture was added. If compost was used as the inoculum, 64 g dry compost was suspended in 64 mL of water, and then inoculated into 80 mL yeast waste medium. Every experiment was triplicate.

Hydrogen-Producing Capacity Test of *Clostridium* Microbes

*C. beijerinckii* L9 (○), *C. diolis* Z2 (Δ) *C. roseum* Z5-1 (⋈) and *C. roseum* W8 (□) cultures were added into 80 mL of (a) a sterile and anaerobic yeast waste medium or (b) a non-sterile and non-anaerobic yeast waste medium, respectively, and shook at 200 rpm and 40° C. under a nitrogen environment to perform a batch fermentation culture. The produced-hydrogen accumulation curve is shown in FIG. 1 (*a*) and (*b*).

From FIG. 1, it was known that the volume of hydrogen produced by *C. beijerinckii* L9 was larger than that by other *Clostridium* microbes. As *C. beijerinckii* L9 was cultured alone, the produced-hydrogen accumulation volume within 100 hours reached 60-70 mL when the yeast waste was sterile and anaerobic, or the produced-hydrogen accumulation volume within 100 hours reached 40-50 mL when the yeast waste was non-sterile and non-anaerobic.

In summary, *C. beijerinckii* L9 has an excellent hydrogen-producing capacity in the above-mentioned sterile or non-sterile yeast waste medium; nevertheless, it also has a distinguished hydrogen-producing capacity over other bacteria in the artificial PYG medium (data not shown).

Figure 2:
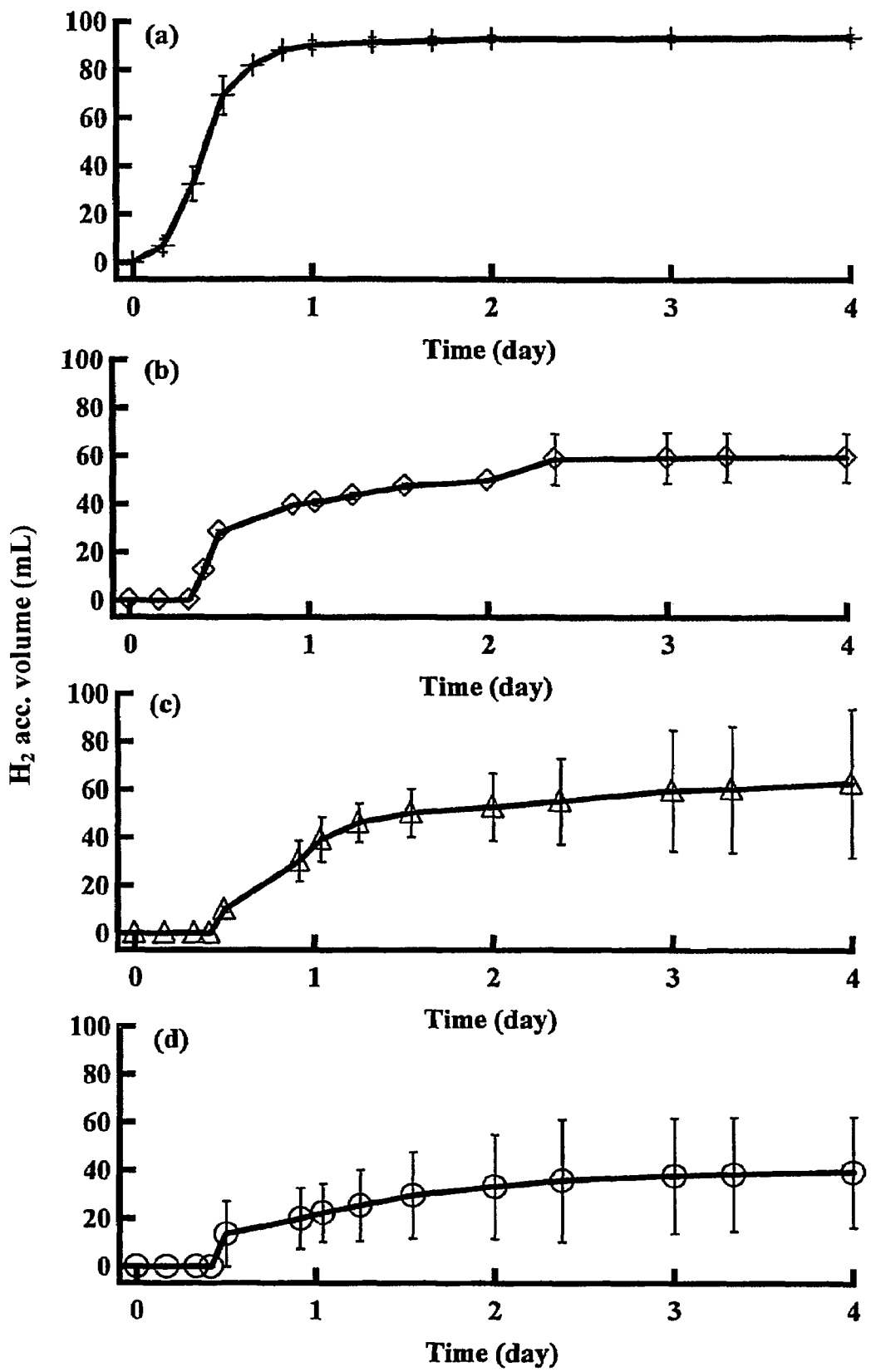
FIG. 2 shows that *C. beijerinckii* L9 and *B. thermoamylovorans* I co-cultured in a yeast waste medium under a sterile and anaerobic environment produce a large amount of hydrogen steadily.

*C. beijerinckii* L9 and *B. thermoamylovorans* I Co-Cultured in Yeast Waste Medium Under a Sterile and Anaerobic Environment Produce a Large Amount of Hydrogen Steadily As shown in FIG. 2, four experiments were designed as below: (a) adding *C. beijerinckii* L9 and *B. thermoamylovorans* I into 80 mL of sterile and non-anaerobic yeast waste medium for a batch fermentation culture; (b) adding *C. beijerinckii* L9 into 80 mL of sterile and anaerobic yeast waste medium for a batch fermentation culture; (c) adding compost into 80 mL of non-sterile and non-anaerobic yeast waste medium for a batch fermentation culture; and (d) using non-sterile and non-anaerobic yeast waste medium for a batch fermentation culture without adding any bacteria.

From the result of the experiments in triplicate shown in FIG. 2(*d*), it was found that the hydrogen production was not stable, and the produced-hydrogen accumulation volume within 100 hours was approximately 40 mL. This result showed that there were hydrogen-producing microbes present in the non-sterile yeast waste medium, but their produced-hydrogen accumulation was lower than the group (c) in which compost was added as the inoculum (and the produced-hydrogen accumulation volume within 100 hours was approximately 60 mL). This result also showed that the inoculum was helpful for promoting the hydrogen-producing capacity of the system.

In addition, when *C. beijerinckii* L9 was added into a non-sterile and non-anaerobic yeast waste medium (see FIG. 1(*b*)) or a sterile and anaerobic yeast waste medium (see FIG. 1(*a*)) for a batch fermentation culture under the above-mentioned conditions, it was found that the produced-hydrogen accumulation volume of the former group within 100 hours was approximately 50 mL, which was lower than the hydrogen volume of the culture in a sterile and anaerobic yeast waste medium, higher than the hydrogen volume of the group shown in FIG. 2(*d*) (about 40 mL) which directly used a sterile yeast waste medium for culture without adding any inoculum, and equal to the hydrogen volume of the group using the compost as the inoculum. Briefly, using a pure-culture inoculum to substitute the compost positively promotes the bacteria storage and the stability of the fermentation chamber operation. This means that *C. beijerinckii* L9 is a predominant hydrogen-producing bacterium over other microbes, and it effectively promotes the hydrogen-producing efficiency. However, if the yeast waste medium is non-sterile and non-anaerobic, the hydrogen production is not as stable as the group using a sterile and anaerobic yeast waste medium (data not shown). This pure anaerobic bacterial system has a predominant culture and a better hydrogen production even when a non-sterile and non-anaerobic yeast waste medium is used. So it can be deduced that the "non-anaerobic yeast waste medium" may produce an anaerobic environment suitable for *Clostridium* microbes by other microbes present in the medium.

As the result shown in FIG. 2(*a*), the produced-hydrogen accumulation volume of this system within 100 hours was 92 mL, and the hydrogen production was stable. And, the hydrogen production and stability of this system were both obviously better than that by using *C. beijerinckii* L9 alone or the compost as the inoculum. In addition, this result also showed that *C. beijerinckii* L9 and *B. thermoamylovorans* I formed an excellent symbiosis system.

Figure 3:
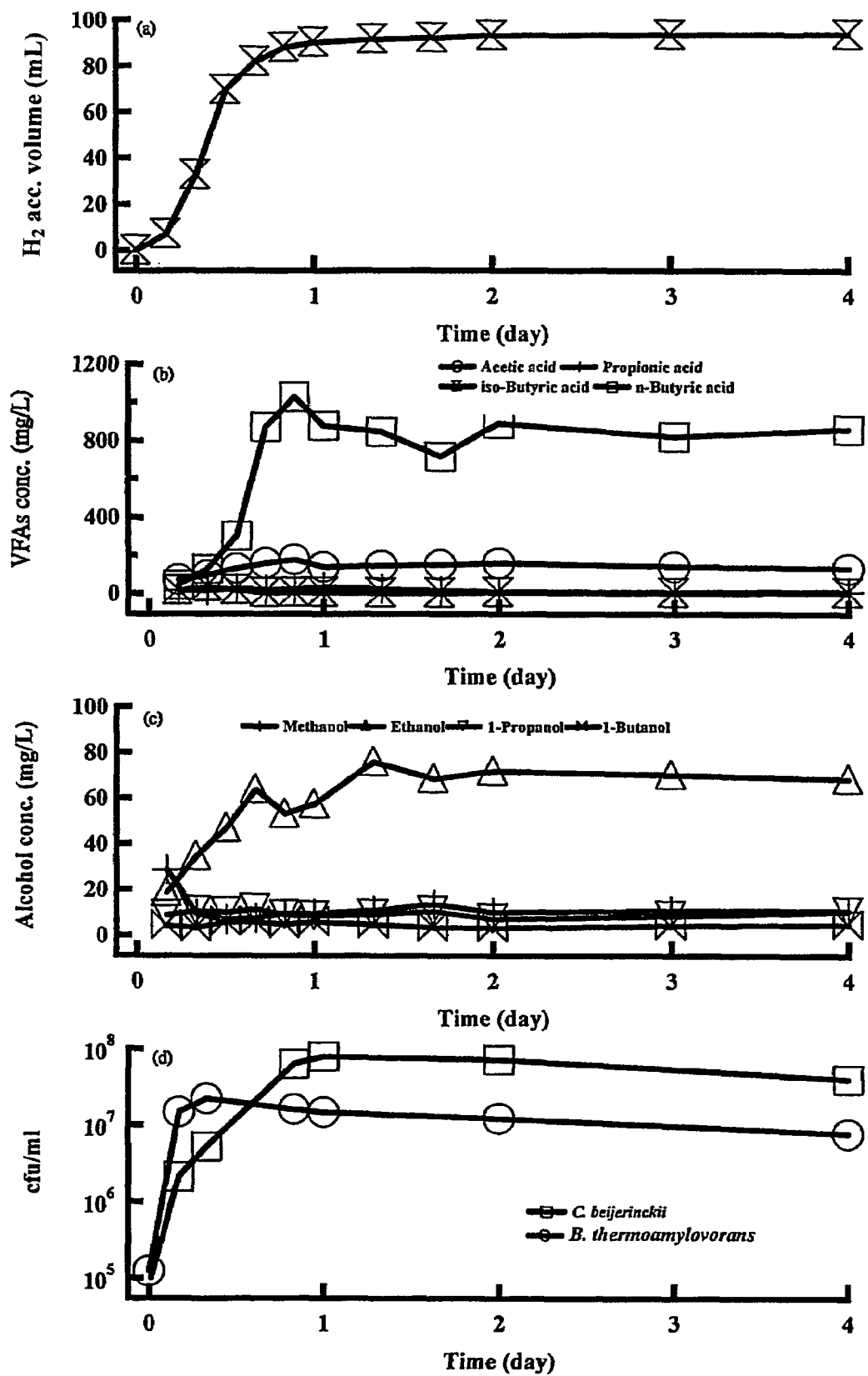
FIG. 3(*a*) shows the produced-hydrogen accumulation volume obtained from *C. beijerinckii* L9 and *B. thermoamylovorans* I co-cultured in yeast waste medium under a sterile and non-anaerobic environment.

From above, we know that adding *C. beijerinckii* L9 alone can have a higher produced-hydrogen accumulation volume than adding the usual compost as the inoculum; therefore, *C. beijerinckii* L9 has a higher potential for the development of a microbial agent suitable for the hydrogen production using yeast waste medium. But *Clostridium* microbes are obligate anaerobes; therefore, in order to have a stable hydrogen production by culturing *C. beijerinckii* L9 alone, the culture medium must be subjected to a complicated anaerobic treatment. Thus, the applicants further added *B. thermoamylovorans* I to co-culture these two bacteria. Although *B. thermoamylovorans* I has no hydrogenase expression, it is one of the bacteria predominant in number in the conventional hydrogen-producing system. Moreover, it is the one having a high decomposition enzyme activity to decompose the large molecules, i.e. yeast waste powder, to small molecules, i.e. nutrient substances. Therefore, it provides more nutrient to *C. beijerinckii* L9 and help the hydrogen production. Yet, most of *Bacillus* microbes are facultative anaerobes and they grow better under an environment comprising oxygen. Thus, when they are co-cultured with *C. beijerinckii* L9, even when a non-anaerobic yeast waste medium is used, the *Bacillus* microbes consume the oxygen in the system and make an anaerobic environment suitable for *Clostridium* microbes to perform hydrogen-producing fermentation. As shown in FIG. 3(*d*), the number of *B. thermoamylovorans* I dramatically increased during the initial stage of fermentation, after that, the number of *C. beijerinckii* L9 increased and hydrogen produced. Accordingly, the present invention provides a fermentation system co-culturing at least one *Clostridium* microbe and at least one *Bacillus* microbe, and these two microbes form an excellent symbiosis system to overcome the defects of conventional hydrogen production using compost or one single bacterium as the inoculum, and promote hydrogen-producing efficiency.

Additionally, in order to analyze the metabolic pathway of the hydrogen production of the present invention, the produced-hydrogen accumulation curve was determined when *C. beijerinckii* L9 and *B. thermoamylovorans* I co-cultured in yeast waste medium under a sterile and non-anaerobic environment, as shown in FIG. 3(a), and other products such as organic acids (ex. volatile fatty acids), organic alcohols, and the like (see FIG. 3(b) and (c)) were also determined. Also, the culture was spread out to observe the changes of cell number and hydrogenase activity during every stage of hydrogen production (data not shown), and it was found that C. beijerinckii L9 grew massively in the initial stage of fermentation, which produced energy by the anaerobic fermentation of glucose. In this metabolic pathway, butanoic acid was produced, and energy and hydrogen were also produced through the electron transfer chain. The ethanol produced in the metabolic process might be produced by C. beijerinckii L9 and B. thermoamylovorans I.

Figure 4:
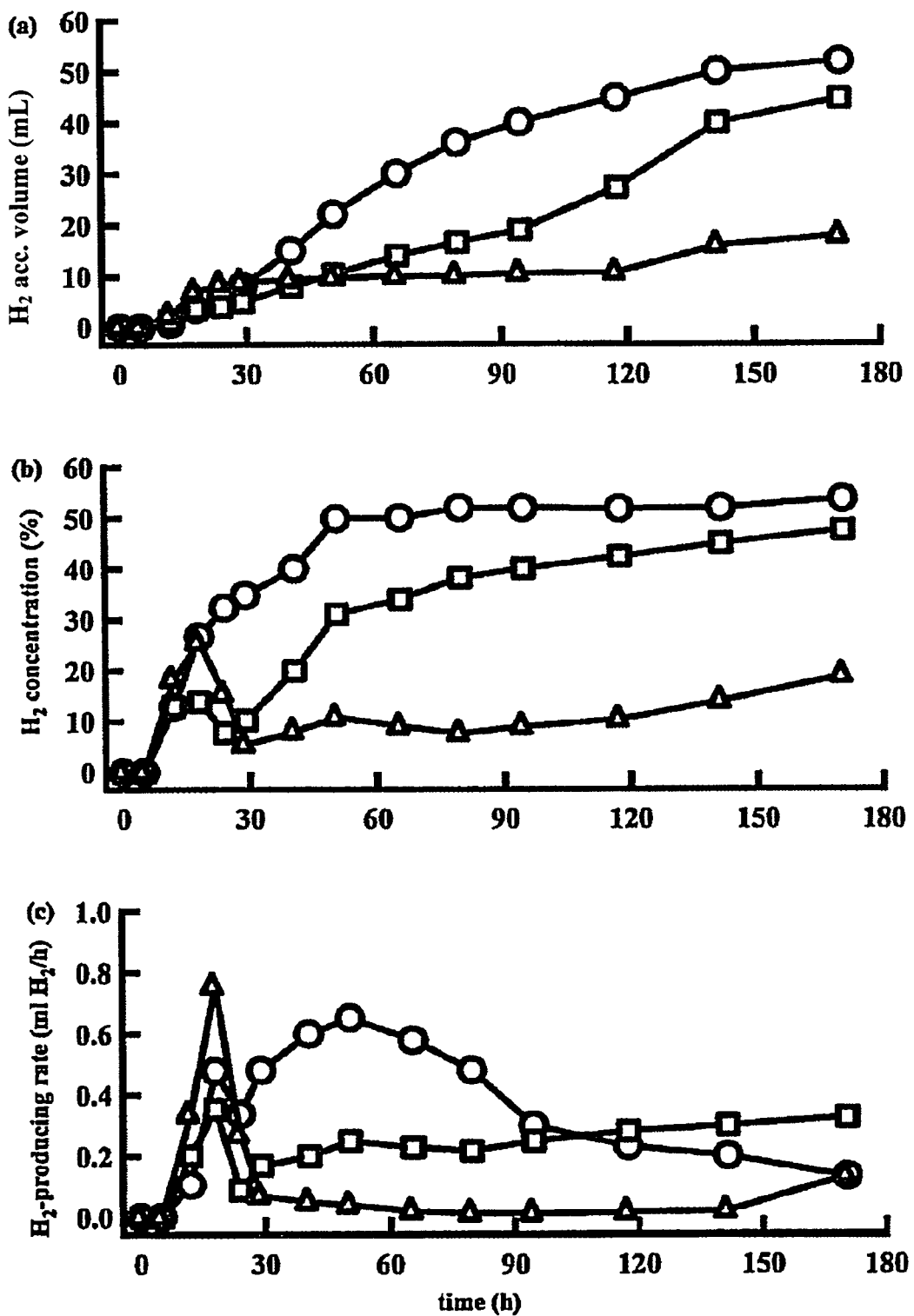
FIG. 4 shows that the short-term hydrogen-producing capacity of *C. butyricum* M1 is greater in a sterile and anaerobic yeast waste medium.
Figure 5:
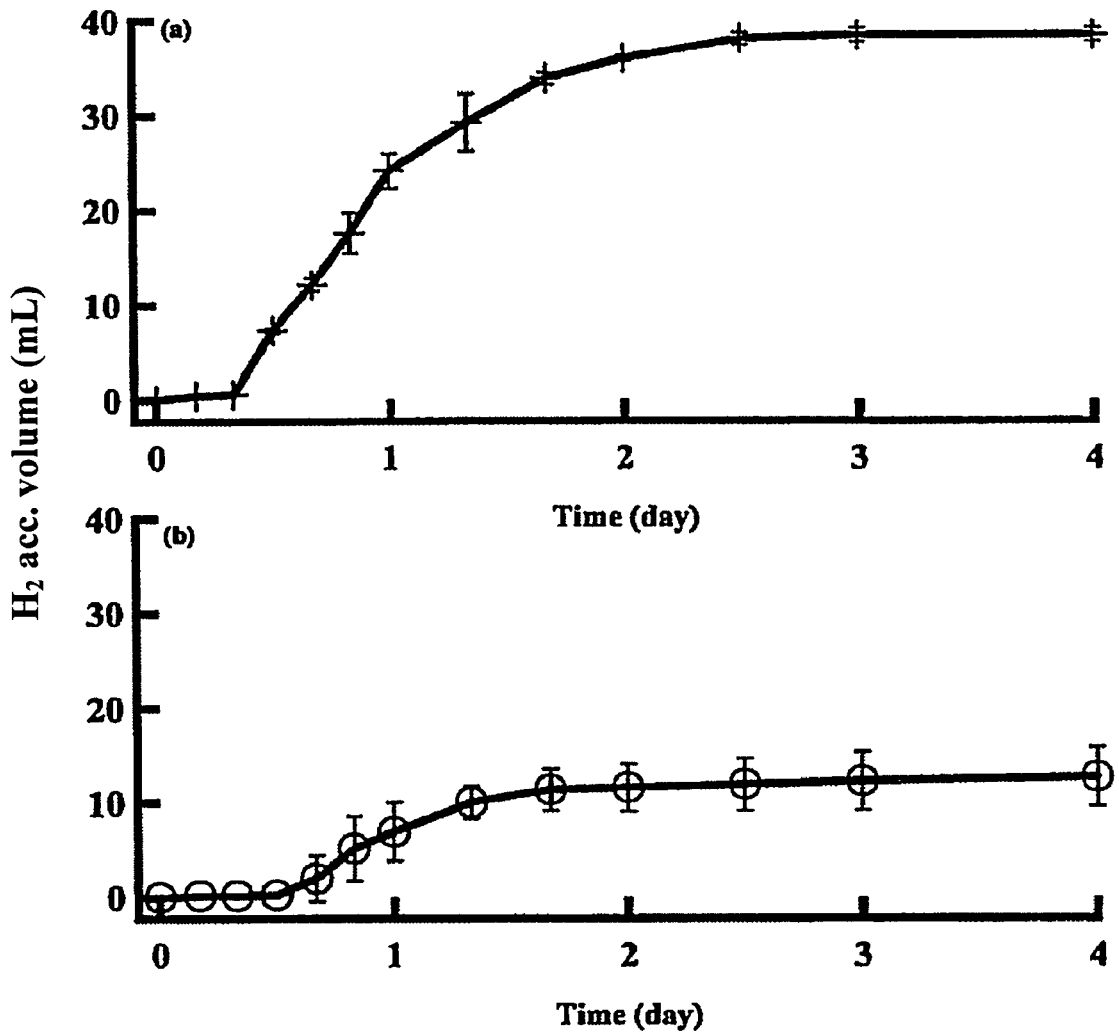
FIG. 5(*a*) shows the produced-hydrogen accumulation curve obtained from *C. butyricum* M1 and *B. thermoamylovorans* I co-cultured under a sterile and anaerobic environment.

Furthermore, another Clostridium microbe, C. butyricum M1, is not predominant in number in the fermentation system of yeast waste medium, but its hydrogenase gene is highly expressed. As shown in FIG. 4, the following conditions were compared: culturing *C. butyricum* M1 alone in a sterile and anaerobic yeast waste medium for a batch fermentation culture (○); adding compost in a sterile and anaerobic yeast waste medium for a batch fermentation culture (□); and using a sterile and anaerobic yeast waste medium for a batch fermentation culture without adding any additional bacteria (Δ).

At hour 40, the hydrogen concentration of the system culturing *C. butyricum* M1 alone was 40% (see FIG. 4(*b*)) and the hydrogen-producing rate of this system was 0.6 mL $H_2$/hour (see FIG. 4(*c*)), and both values are two times higher than that of the system using compost as the inoculum. However, when the time extended to 100 hours, the raise of produced-hydrogen accumulation volume slowed down, and the maximum volume, about 50 mL, was reached at hour 180 (see FIG. 4(*a*)). This result shows that although *C. butyricum* M1 is not predominant in number in the fermentation system of yeast waste medium, but it can dramatically enhance the produced-hydrogen volume in a short time. In addition, *C. butyricum* M1 has a lower hydrogen production in artificial PYG medium and yeast waste medium than *C. beijerinckii* L9 (data not shown), but the lag phase of *C. butyricum* M1 is only 2-3 hours, which is shorter than the 10 hours of *C. beijerinckii* L9.

FIG. 5 shows the produced-hydrogen accumulation curve obtained from (a) *C. butyricum* M1 and *B. thermoamylovorans* I co-cultured, or (b) *C. butyricum* M1 cultured alone in a sterile and non-anaerobic yeast waste medium for a batch fermentation culture. At hour 96, the produced-hydrogen accumulation of the co-culture group is about 40 mL (see FIG. 5(*a*)), which is about 3 times higher than that of the group that *C. butyricum* M1 cultured alone (see FIG. 5(*b*)). The result presents that *C. butyricum* M1 and *B. thermoamylovorans* I can form an excellent symbiosis system, that is to say, *C. butyricum* M1 can use the simple nutrient resource produced from the decomposition of yeast by *B. thermoamylovorans* I.

REFERENCES

1. Chang J J, Chen W E, Shill S Y, Yu S J, Lay J J, Wen F S, Huang C C Molecular detection of the clostridia inan anaerobic biohydrogen fermentation system by hydrogenase mRNA-targeted reverse transcription-PCR. *Appl Microbial Biotechnol* 70:598-604, 2006
2. E. De Clerck, t. Vanhoutte, T. Hebb, J. Geerinek, J. Devos and P. De Vos Isolation, characterization and identification of bacterial contaminants in semifinal gelatin extracts. *Applied and Environmental Microbiology*, June 2004, p. 3664-3672.
3. Ezeji T, Qureshi N, Blaschek H P. Butanol production from agricultural residues: impact of degradation products on *Clostridium* beijerinckii growth and butanol fermentation. *Biotechnol Bioeng.* 2007 Feb. 1 [Epub ahead of print]
4. David J. Lane, Bernadette Pace, Gary J. Olsen, David A. Stahl, Mitchell L. Sogin, and Norman R. Pace Rapid determination of 16S ribosomal RNA sequences for phylogenetic analysis. *Proc. Natl. Acad. Sci. USA* Vol. 82, pp. 6955-6959, October 1985
5. V. N. Ivanov, J.-Y. Wang, O. V. Stabnikova, S. T.-L. Tay and J.-H. Tay Microbiological monitoring in the biodegradation of sewage sludge and food waste. *Journal of Applied Microbiology* 2004, 96, 641-647.
6. Lay J J Modeling and optimization of anaerobic digested sludge converting starch to hydrogen. *Biotechnol Bioeng* 68(3): 269-278, 2000
7. Lay J J Biohydrogen generation by mesophilic anaerobic fermentation of microcrystalline cellulose. *Biotechnol Bioeng* 74(4): 280-287, 2001
8. Shaheen R, Shirley M, Jones D T. Comparative fermentation studies of industrial strains belonging to four species of solvent-producing clostridia. *J Mol Microbial Biotechnol* 2000 January; 2(1): 115-24.
9. Jing-Yuan Wang, Olena Stabnikova, Stephen Tiong-Lee Tay, Volodymyr Ibanov and Joo-Hwa Tay Intensive bioconversion of sewage sludge and food waste by *Bacillus* thermoamylovorans. *World Journal of Microbiology & Biotechnology* 19: 427-432, 2003

What is claimed is:

1. A microbial hydrogen-producing process, comprising:

providing at least one *Clostridium* microbe and at least one *Bacillus* microbe; and co-culturing said at least one *Clostridium* microbe and said at least one *Bacillus* microbe in a fermentation culture system;

wherein said process produces hydrogen.

2. The process according to claim 1, wherein said at least one *Clostridium* microbe comprises *C. beijerinckii* L9 deposited with Food Industry Research and Development Institute under the accession number BCRC910361 on Jul. 27, 2007 or *C. butyricum* M1 deposited with Food Industry Research and Development Institute under the accession number BCRC910362 on Jul. 27, 2007.

3. The process according to claim 1, wherein said at least one *Bacillus* microbe is *B. thermoamylovorans* I deposited with Food Industry Research and Development Institute under the accession number BCRC910360 on Jul. 27, 2007.

4. The process according to claim 1, wherein said fermentation culture system is a fermentation system having a sterile and anaerobic environment and using an organic waste medium.

5. The process according to claim 4, wherein said organic waste medium is a medium produced from yeast waste, distillers grains, kitchen waste, sewage sludge, agricultural waste, molasses and its fermented waste liquid, energy crop, algae, or mixtures thereof.

6. The process according to claim 4, wherein said anaerobic environment is formed by the interaction between said at least one *Clostridium* microbe and said at least one *Bacillus* microbe.

7. The process according to claim 1, wherein fermentation is performed at 35-45° C. in said fermentation culture system.

8. A microbial hydrogen-producing process, comprising:
co-culturing at least one *Clostridium* microbe and at least one *Bacillus* microbe in a medium produced from yeast waste under an anaerobic environment in a fermentation system, wherein said process produces hydrogen.

9. The process according to claim 8, wherein said fermentation system is further a fermentation system having a sterile environment.

10. The process according to claim 8, wherein said at least one *Clostridium* microbe comprises *C. beijerinckii* L9 or *C. butyricum* M1.

11. The process according to claim 8, wherein said at least one *Bacillus* microbe is *B. thermoamylovorans* I.

12. The process according to claim 8, wherein said anaerobic environment is formed by the interaction between said at least one *Clostridium* microbe and said at least one *Bacillus* microbe.

* * * * *